United States Patent [19]
Nassif

[11] Patent Number: 5,562,615
[45] Date of Patent: Oct. 8, 1996

[54] FREE FLOW DETECTOR FOR AN ENTERNAL FEEDING PUMP

[75] Inventor: George A. Nassif, Palatine, Ill.

[73] Assignee: Corpak, Inc., Wheeling, Ill.

[21] Appl. No.: 188,637

[22] Filed: Feb. 28, 1994

[51] Int. Cl.$^6$ ................................................ A61M 31/00
[52] U.S. Cl. ........................... 604/67; 604/65; 604/247; 604/253; 128/DIG. 13
[58] Field of Search ............................. 604/65, 67, 246, 604/248, 251, 253, 250, 247, 254, 255, 245; 128/DIG. 12, 13

[56] References Cited

U.S. PATENT DOCUMENTS

| | | |
|---|---|---|
| 3,230,767 | 1/1966 | Heigl et al. . |
| 3,873,814 | 3/1975 | Mirdadian . |
| 4,256,437 | 3/1981 | Brown . |
| 4,278,085 | 7/1981 | Shim . |
| 4,487,604 | 12/1984 | Iwatschenko et al. . |
| 4,498,843 | 2/1985 | Schneider et al. .......................... 417/22 |
| 4,515,584 | 5/1985 | Abe et al. . |
| 4,518,327 | 5/1985 | Hackman . |
| 4,636,144 | 1/1987 | Abe et al. . |
| 4,832,584 | 5/1989 | Nassif . |
| 4,884,013 | 11/1989 | Jackson et al. . |
| 4,913,703 | 4/1990 | Pasqualucci et al. . |
| 5,017,192 | 5/1991 | Dodge et al. ............................ 604/250 |
| 5,251,027 | 10/1993 | LaBeau . |
| 5,300,044 | 4/1994 | Classey et al. ...................... 604/256 X |
| 5,374,251 | 12/1994 | Smith ....................................... 604/151 |

OTHER PUBLICATIONS

FLEXIFLO Companion Enteral Nutrition Pump Operating Manual, Aug. 1987, Ross Laboratories.
FLEXIFLO–III Enteral Nutrition Pump Operating Manual, Aug. 1985, Ross Laboratories.
FLEXIFLO QUANTUM Enteral Pump Operating Manual, 1992, Ross Laboratories.
KANGAROO 324 Feeding Pump Operating Manual, 1991, Sherwood Medical Company.
KM–80 Enteral Feeding Pump Operating Instructions, O'Brien.
Corpak Enteral Feeding Pump, Model 300 D, Operating Manual, 1989, Corpak, Inc.
Corpak Enteral Feeding Pump, Model VTR 300, Operating Manual, 1987, Corpak, Inc.

Primary Examiner—Corrine M. McDermott
Assistant Examiner—N. Kenti Gring
Attorney, Agent, or Firm—Wallenstein & Wagner, Ltd.

[57] ABSTRACT

An enteral fluid infusion system wherein fluid is pumped through a conduit from a fluid supply source to a patient by a rotary peristaltic pump operating in an intermittent duty cycle mode which includes a free flow detector. The free flow detector includes a sensor for the operation of the peristaltic pump, as for example by the rotation of the rotor and/or motor; a sensor for the flow of fluid in the conduit. The free flow detector compares the sensed operation of the pump with the sensed flow against predetermined criteria. During operation of the fluid infusion system, if flow is sensed when the pump is not operating, as determined by the fact that no rotation is occurring, an alarm will be initiated to indicate that a free flow condition exists.

17 Claims, 2 Drawing Sheets

FREE FLOW DETECTOR FOR AN ENTERNAL FEEDING PUMP

DESCRIPTION

1. Technical Field of the Invention

This invention relates generally to a reliable and economical system for the enteral delivery of nutritional and/or medical fluids by means of a pump from a source of supply, such as a bag, through a conduit means, such as a tube, into a patient, and more particularly concerns a free flow detecting means for a pump operating in an intermittent duty cycle mode. The free flow detecting means includes the combination of a fluid flow monitoring means, a pump rotation sensing means and a controller means providing a reliable, economical and convenient means to detect a "free flow" condition of fluid flowing through the tube when the pump is not pumping fluid.

2. Background of the Invention

In the treatment of certain diseases and conditions such as where patients cannot eat normally, it is required that periodic and controlled amounts of enteral nutritional fluids and/or medical fluids be administered and infused into the patient in accordance with a predetermined dosage schedule. Various systems have been provided to accomplish enteral infusion. These systems typically include a fluid supply means such as bags that act as reservoirs to hold the fluids to be infused, delivery pumps of various types and operating modes, and conduit means such as flexible tubes that convey the fluids to be administered from the supply means, through the pumps to and into the patient. Each of the various systems accomplish the infusion task with varying degrees of success and reliability.

One such infusion pump means is a rotary peristaltic pump wherein a plurality of tube engaging means such as rollers are attached in generally equal spacing around the periphery of a rotor means. A flexible tube carrying the fluid to be infused extends around a portion of the periphery of the rotor means and is held against the tube engaging means or rollers such that the rollers squeeze the flexible tube member together and isolate the fluid in the tube between the adjacent pairs of rollers. Accordingly, as the rotor means is rotated the rollers squeeze the tube together and force the predetermined amount of isolated fluid to be moved along and through the tube by the squeezing action. The pumps rotate so that the fluid, typically under pressure of gravity, flows from the reservoir to the pump and is moved by the pump to the patient in predetermined amounts and rates. A control means allows exact settings to be made and monitored. Pumps of this nature are well known in the medical environment because they allow fluid to be pumped in a way that the fluid does not contact any portions of the pump means outside of the tube in which it is flowing whereby fluids may be safely pumped without fear of contamination and whereby, the tube and fluids may be quickly changed without cleaning the pump means and delivered in a controlled manner. Also, the pumps are capable of providing accurate amounts of the fluid to be delivered through the tube for each rotation of the rotor.

Operation of enteral infusion pumps generally will be in either a continuous or intermittent manner. Pumps that operate in a continuous manner run constantly but at various speeds whereby the flow through the pump is a function of the pump speed. In pumps that run in an intermittent manner, the motor operates at a constant speed for predetermined periods of time or duty cycles whereby the flow is varied based on the length of time the pump is not running or in what is called an "idle" mode. Each of the types of pumps and operating modes provide for audible and/or visible alarms to alert personnel of various conditions that may occur, such as for example, occlusions wherein the conduit is blocked or flow restricted at some point; completion of the prescribed dosage; a power supply failure, such as low battery; and other conditions.

A potential problem with rotary peristaltic pumps is that the tubing can be improperly initially secured to the rotor or may become disengaged for some reason. If either of these conditions occur, the rotor will no longer block flow and with a gravity supply of fluid, fluid will begin to flow freely through the tube. As may be understood, in this "free flow" condition, the amount of fluid passing through the tube is no longer a function of the predetermined rotation of the pump, but rather a function of the fluid pressure and the variable and unknown cross-sectional open flow interior diameter of the tube. Where the dosage being fed must be closely controlled, the uncontrolled "free flow" condition could be dangerous under certain circumstances. In a peristaltic pumping mechanism where the pump rotor is running constantly, a flow detecting means may not accurately detect the difference between fluid flow resulting from disengagement of the flexible tubing from the rotor or whether the flow is resulting from the normal operation of the pump. On the other hand, in an intermittent or bolus pumping system, no fluid should be flowing through the tube while the pump rotor is not turning and if flow is detected during this time, a free flow condition exists.

Accordingly, there is a need for a means for detecting the presence of a "free flow" condition during the "off" mode of an intermittent medical infusion pump.

Although the use of peristaltic pumps for enteral delivery of fluids is known in the prior art as shown for example in the U.S. Pat. Nos. 4,487,604; 4,498,843; 4,518,327; 4,515,584; 4,636,144; 4,832,584; 4,884,013; 4,913,703 and 5,251,027; none of these in applicant's opinion, provide an economical and convenient means for detecting free flow conditions. The latter two patents provide a magnetic emitter/sensor arrangement between predetermined portions of the tube and the motor whereby if the tube is not in its predetermined position, the motor will be disabled. This however is not considered a true free flow detector since it may be inadvertently or intentionally circumvented. Thus, the sensor will pick up any magnetic field even if the tube is not in place so that if the free flow occurs in a situation where a magnetic field is present, the condition will not be detected.

Thus, there is a need for a simple, reliable means to measure rotation of the pump rotor whereby if fluid is flowing and the pump is in the "off" condition during an intermittent operating mode, an appropriate alarm and/or fail safe conditions will be initiated.

Other approaches to the problem of detecting a free flow condition known to applicant include the provision of various means for guiding or entrapping the tube to keep it in place around the rotor and reduce the possibility of the tube disengaging itself. These are shown for example in the U.S. Pat. Nos. 4,278,085 and 4,256,437. Such means include spring loaded levers and other relatively complex mechanical means which typically are not only expensive, but increase the amount of time necessary to change the tubing between patients.

Another type of means for detecting free flow includes the measurement of drops of fluid flowing and comparing these to the number of drops which should be flowing to achieve the proper dosage. If the number of drops is outside of a predetermined limit range, an alarm will sound. This method is complex and subject to variations in the size and formation of the drops caused by differences in formula of the fluid being pumped.

SUMMARY OF THE INVENTION

The deficiencies of the prior art are overcome by an enteral fluid infusion system wherein fluid is pumped through a conduit means from a fluid supply source to a patient by a rotary peristaltic pump operating in a bolus mode and a free flow detector means in the system compares flow conditions in the conduit means with the operating condition of the pump to detect any possible "free flow" condition. Thus, if a flow is detected when the pump is not operating, an appropriate alarm will be activated. This assures that if the tube means becomes disengaged from the rotor for any reason and flow is due to gravity rather than pump rotation, the condition will be detected and an alarm activated.

Accordingly, it is an object of the present invention to provide an enteral infusion system including an economical and reliable means to detect the occurrence of a free flow of fluid in the system tubing during the "off" condition of a rotary peristaltic pump operating in an intermittent mode.

It is a further object of the invention to provide a simple and reliable "free flow" detection means for an enteral infusion system including a pump rotation sensing means for determining if the pump is rotating and should be pumping fluid; a fluid sensing means for detecting the flow of fluid in the system; and a microprocessor means for comparing the conditions sensed against a predetermined program to determine whether a free flow condition exists and if so, to initiate appropriate alarms.

Another object of the invention is to provide an enteral infusion system in a compact, durable housing that is easy to use.

Yet another object of the present invention is to use the period of the pump operation when the rotor is not turning for a pump means operating in an intermittent mode and compare it to the flow condition in the conduit means during this period to provide an economical and reliable means for detecting a free flow condition.

Other features and advantages of the invention will be apparent from the following specification taken in conjunction with the following drawings.

DETAILED DESCRIPTION OF A PREFERRED EMBODIMENT

Figure 1:
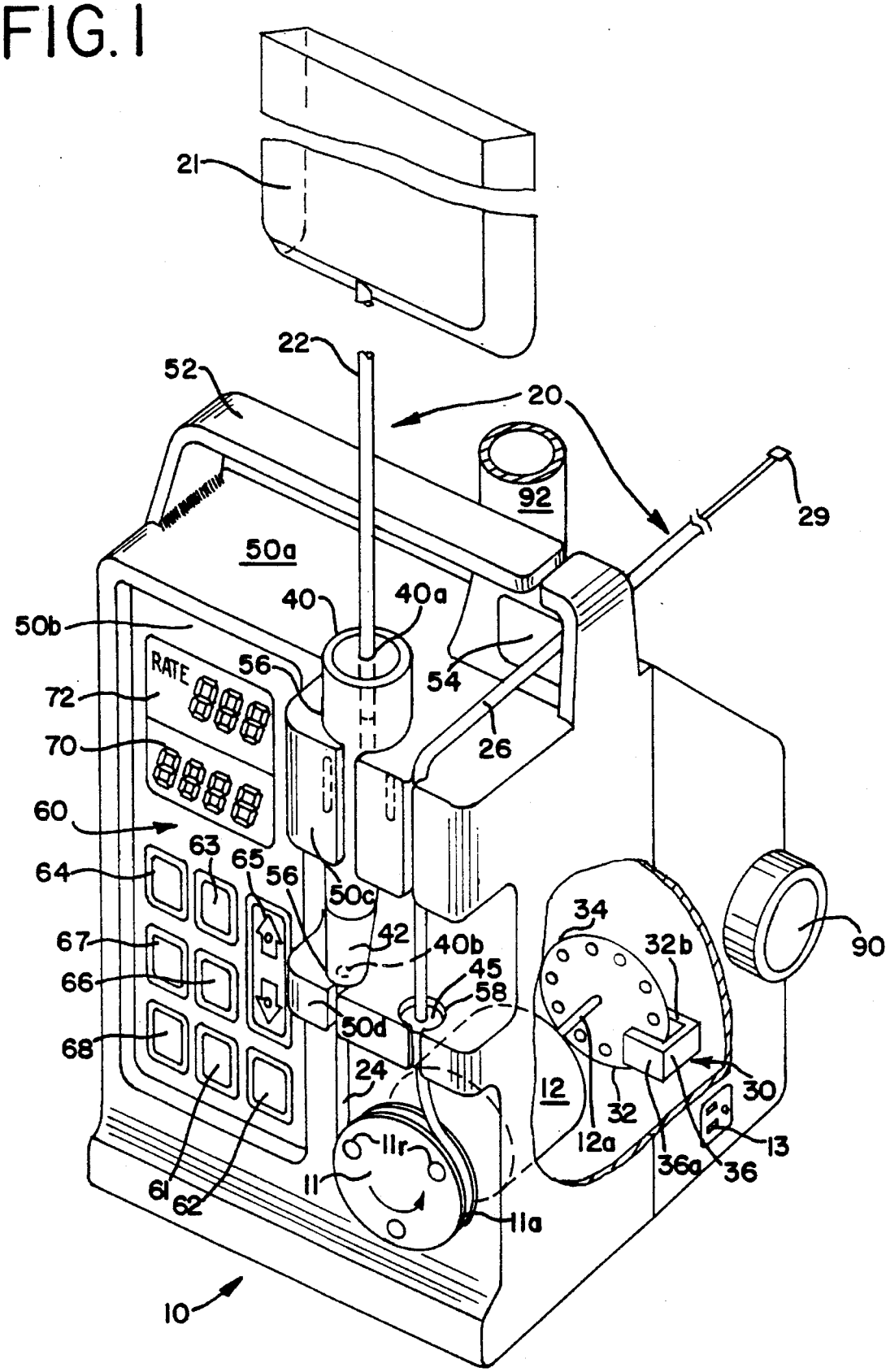
FIG. 1 is a perspective view of a preferred embodiment of the invention.

While this invention is susceptible of embodiments in many different forms, there is shown in the drawings and will herein be described in detail, preferred embodiments of the invention with the understanding that the present disclosure is to be considered as an exemplification of the principles of the invention and is not intended to limit the broad aspects of the invention to the embodiments illustrated.

Figure 2:
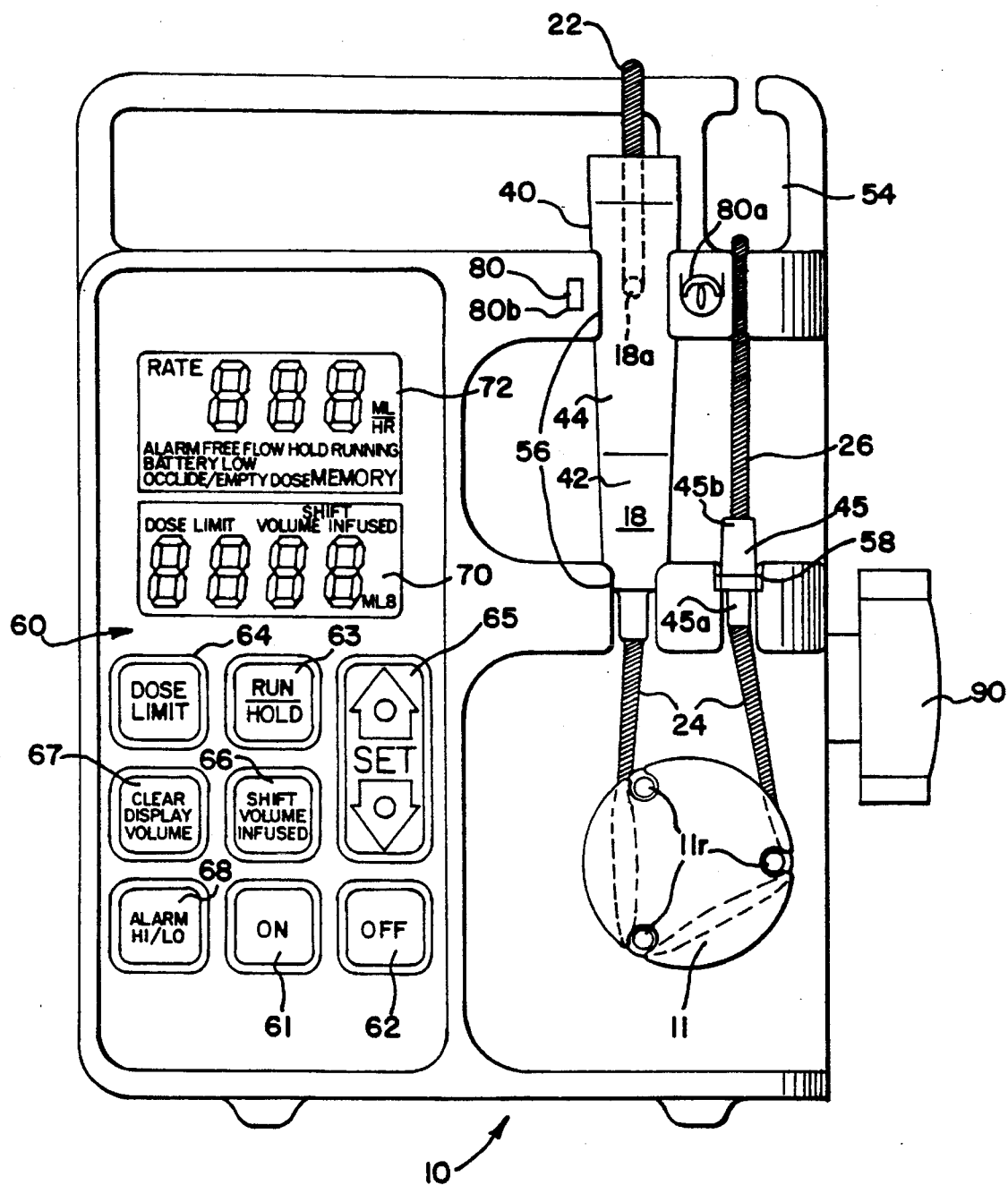
FIG. 2 is an elevational view of the front of the invention shown in FIG. 1.

A preferred embodiment of the invention as shown in FIGS. 1 and 2 includes an electrically driven peristaltic pump means generally indicated at 10 located intermediate the ends of a conduit means such as a tube means generally indicated at 20 that extends from a fluid supply means schematically indicated at 21 to a fluid receiver location 29. The pump means 10 pumps a fluid 18 through the tube means 20. The tube means 20 as shown in the preferred embodiment, includes three sections or portions between the fluid supply means and the receiver location. These are a first section or portion 22 connected to and extending between the fluid supply means which may be in the form of a well known enteral fluid bag 21 located above the pump means 10, and an inlet side 40a of a first or site chamber means generally indicated at 40; a second tube section or portion 24 extending from an outlet side 40 of the site chamber means 40 and around a portion of the periphery 11a of a rotor 11 of the pump means 10 to an inlet side of 45a of a second or pump set connector means 45; and a third section or portion 26 extending from an outlet side 45b of the pump set connector means 45 to a fluid receiver location 29. The fluid receiver will be a patient not shown. Typically enteral fluids are received by the patient through the nose, the mouth or stomach.

The rotor 11 is driven by a suitable motor means 12 such as an electric motor. The motor may be of a direct drive or stepper motor design. The electric motor may be powered by 110 volt house current and/or a 7.2 volt battery or other suitable electric source of electricity. In practice the battery is provided as a fail-safe backup to the house current In the preferred embodiment the second section 24 of the tube means 20 is in pumping engagement with a portion of the periphery 11a of the rotor 11 so that during operation of the pump, the tube means 24 bears against the rollers in the portion of the periphery with which it is in engagement. The rotor 11 includes at least three tube engaging means such as rollers 11r. The rollers 11r each compress the tube means 24 so that no significant amount of fluid can pass therethrough at the point of contact whereby as the rotor rotates and brings two rollers 11r into contact with the tube, a predetermined amount of fluid 18 will be trapped between the points of contact of adjacent rollers. As the rollers are moved along the tube portion 24, in the direction shown by the arrow, the trapped fluid 18 is moved in the direction of rotation from the supply side to the delivery side. Looking at FIG. I the rotor 11 and rollers 11r move in a counterclockwise direction to force fluid under pressure from the second section 24 through second connector 45 into section 26 and on to the receiver location 29.

At the same time, the pumping action draws fluid 18 from a reservoir 42 at the bottom of the site chamber means 40. The site chamber means 40 also includes a drip chamber 44 in which the fluid 18 forms into a sequence of drops 18a on an end extension 22a of the tube section 22. Each drop 18a drips from extension 22a one drop at a time as the fluid 18 passes through first connector 40 from supply source 21 through tube section 22. As each drop 18a forms on extension 22a it is sensed by a flow detector means generally indicated at 80. As may be best seen in FIG. 2, the drip detector means 80 includes a light emitter 80a and a light sensor 80b positioned so that the drop 18a on the extension 22a interrupts the light passing between 80a and 80b whereby the presence of each drop 18a is detected. The drops 18a fall into reservoir 42 from which they are drawn by the pump. Proper positioning of the extension end 22a relative to sensor means 80 whereby drop formation is effectively sensed, is assured by proper configuring of the outer shape of site chamber means 40 and the mating first support means therefor generally indicated at 56. A mating inverted frusto conical shape of the site chamber means 40 and support recess means 56 has been found satisfactory.

As will become clear, each rotation of the rotor implies a certain amount of fluid has been delivered from the supply source 21 to the location 29 of the fluid receiver patient, hence, the motor 12 has attached thereto a rotation monitoring means 30 to easily and accurately monitor the rotation of the motor and the rotor whereby the amount of fluid pumped may be immediately and accurately determined. Various means to perform this motor/rotor rotation monitoring function are old and well known to those skilled in the art. Included among these rotation monitoring means are discs with regularly spaced magnet means thereon that are sensed as they pass a predetermined magnetic field detecting point. Equivalent means include those shown for example in U.S. Pat. Nos. 3,230,767 and 3,873,814 wherein fluid flow is measured by means including discs with regularly spaced optical transmitting means therein such as holes or slots which allow light to be sensed as the disc rotates and the holes or slots pass between a light source and a photoelectric sensing means. A variation employing a reflector in place of the hole or slot is also disclosed in the patents. In practice we have found that locating an optical interrupting means such as a disc 32 connected to an end extension of the motor shaft 12a opposite from the end of the shaft to which the rotor is attached provides a direct indication of rotor movement. In the preferred embodiment the disc 32 has a predetermined number of regularly spaced holes 34 therein whose presence is detected as the disc turns by an optical sensor 36. This provides excellent results. The optical emitting and sensing means 36 may be of a type manufactured by Honeywell of Minneapolis, Minnesota, and include a light transmitter 36a and light sensor 36b. The disc 32 is preferably fixedly connected to the opposite end of shaft 12a from pump rotor 11 so that as the disc 32 spins in direct relationship with rotor 11, the holes 34 will pass between the transmitter 36a and sensor 36b and allow a beam of light to pass therethrough whereby each hole will generate a signal that is counted by the controller means 60 to determine the exact rotation of rotor 11.

A housing means generally indicated at 50 is provided to conveniently enclose and/or support for example the pump means 12, rotation detection means 30, site chamber means 40, pump set connectors 45, portions of the conduit means 20, control means 60, and flow sensor means 80. In practice the housing means 50 is approximately 5-3/8 inches wide, 4-7/8 inches deep, 8 inches high and weighs about 3.75 pounds. It includes an easy-to-grip handle or hanger means 52 on the housing top portion 50a. A tubing retainer means 54 is integral with the handle at one end. A housing front panel 50b includes support bracket means 50c and 50d having a recess means 56 for releasably securing the site chamber means 40, and a second recess means 58 receiving and releasably securing the pump set connector means 45. The site chamber means 40 includes reservoir 42 and drip chamber 44. The front panel further includes the instrumentation portion of the control means 60 and a flow sensing means generally indicated at 80. A suitable vertically disposed recess means in the back panel not shown has a grip adjusting means such as the knob generally indicated at 90. As shown this is advantageously included in a side panel easily accessible from the front and serves as another means to permit attachment of the housing 50 to a pole means 92 or other support means.

The means for securing the pump set connector means 45 may be seen in FIG. 2 to include a recess 58 that receives the connector in generally mating relationship and secures it against disengaging movement. In practice the flexible tube means 24 is stretched over rollers 11r so that the resilience of the tube means 24 will help hold the sit chamber 40 and pump set connectors 45 respectively tightly in the respective support means 56,58. As will be understood, it is possible that if the pump set connector 45 is not properly seated in support 58 or if tube 24 should somehow be too long or become stretched over long use, the connector means 45 may become disengaged from support means 58 and allow the tube means 24 to become disengaged from rotor 11 whereby with rollers 11r no longer squeezing the tube to block the flow of fluid 18a, gravity free flow may result.

Control means 60 includes a microprocessor controlled by software and the various control means 61–68 identified in FIG. 2. Activation of an "on" switch 61 energizes the pump; causes the alarms to be activated for a brief self test period to indicate whether they are working and performs internal diagnostic test. An "off" switch 62 turns the pump off although the battery continues to charge when the unit is running off 110 volt current. All data such as flow rate, volume infused, dose limit and shift volume infused are retained in system memory for 24 hours.

A "run-hold" control 63 initiates pump action in the run mode after a rate is set and is displayed on display means 72. In the "hold" mode the pump is stopped.

When in the "hold" mode, a dose limit control 64 displays the dose limit as shown on a display 70 and activates the "set" touch control to allow input of a specific dose setting. In a "run" mode the control 63 displays the dose limit briefly or as long as held and then automatically returns the display to "volume infused" as shown on display 70.

Other appropriate controls not essential to an understanding of this invention may also be included.

In operation the user turns the pump means "on" uses the "get" switch 65 to select the predetermined rate at which the fluid is to be administered, which will be displayed on display 72, and presses the "run" mode control 63 to initiate administration. With the capacity of the tube 24 between rollers 11r known, the control means 60 causes the rotor 11 to rotate intermittently in predetermined duty cycles to deliver the predetermined quantity of fluid required per period of time to match the rate selected as shown on panel 72. It will be understood that during each duty cycle the rotor is caused by motor 12, as directed by controller 60, to turn a predetermined number of revolutions or portion(s) thereof and pause on idle a predetermined length of time before beginning the next duty cycle. During the pause in each duty cycle the fluid flow sensor means continues to detect flow and if it does detect flow, the "free flow" alarm is initiated. The alarm continues until the "hold" or "off" control is activated.

Under certain conditions the first section of tubing 22 may contain small droplets that coalesce to form a larger drop 18 that may form on extension 22a and would be sensed by the drip detector means 80. Since this could be interpreted as flow by the drip detector sensor 80 and trigger the "free flow" alarm if the motor 12 is not running, the controller means 60 is programmed to ignore the first drop in determining whether a free flow condition exists.

In addition to facilitating detection of flow when the pump is in its "off" position, it has been found that operating the pump means 10 in an intermittent mode, provides lower power consumption and extends the life of the batteries used to power the pump.

With the positive peristaltic volume monitoring means and pump action monitoring means it is not as important where the fluid reservoir source 21 is in relationship to the pump means 10 so long as there is gravity flow. Thus the enteral pump may be used under a wide variety of conditions including being carried by ambulatory patients. The battery makes this possible and also provides a backup in the event the 110 volt power source is interrupted.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein.

I claim:

1. An enteral fluid administration system for the controlled delivery of a fluid to a patient comprising;

a fluid supply containing a predetermined supply of said fluid to be administered;

a tube having a first end connected to said supply to receive said fluid and a second end adapted to deliver said fluid into said patient;

a peristaltic pump having a rotor means engaging said tube intermediate to first and second ends of said tube;

said tube and said rotor means being in a contacting relationship whereby said rotor means normally prevents fluid flow through said tube when said rotor means is not rotating;

said pump having a motor connected to said rotor means to rotate said rotor means intermittently in duty cycles to cause said fluid to be pumped through said tube from said supply to said patient;

a rotation sensing means for determining if said rotor means are rotating;

said rotor means being located at a gravity level below said fluid supply; and a free flow sensor and alarm connected with said rotation sensing means for detecting flow in said tube when said rotor is not rotating and for activating said alarm.

2. An enteral administration system according to claim 1 wherein said tube includes a first connector and a second connector, separated by a rotor engaging section intermediate said first and second ends thereof to divide said tube into three sections;

said rotor engaging section of said tube being wound over said rotor means, a first end of said rotor engaging section being connected through said first connector to the section of said tube having said first end, and a second end of said rotor engaging section being connected through said second connector to the section of said tube having said second end.

3. An enteral administration system according to claim 2 including a housing for securing said pump and supporting said first and second connector, said rotor engaging section of said tube being normally stretched over a portion of said rotor between said first and second connector, said free flow sensor and alarm including a fluid flow detector, said first connector being connected to said fluid flow detector for detecting fluid flowing through said tube at said first connector.

4. An enteral administration system according to claim 3 wherein said housing has first and second support members, said first and second connection being removably connected to said housing at said first and second support members respectively.

5. An enteral administration system according to claim 4 wherein said fluid flow detector includes a drip detector, said first connector having a drip chamber integrally connected therewith, said drip chamber being located at a predetermined location relative to said drip detector whereby drops of fluid flowing through said tube are sensed by said drip detector means.

6. An enteral administration system according to claim 4 wherein said system further includes a microprocessor electrically connected to said rotation-sensing means and to said fluid flow detector to compare data received from said rotation sensing means and said fluid flow detector whereby if fluid is flowing when no rotation is detected an appropriate alarm will be initiated.

7. An enteral fluid infusion system wherein fluid is pumped through a conduit from a fluid supply source to a fluid receiving patient location comprising a fluid supply source; a fluid receiving location; a conduit extending from said fluid supply source to said fluid receiving location; a rotary peristaltic pump rotating in a bolus mode positioned intermediate said supply source and said fluid receiving location; said pump being in operative relationship with said conduit to pump said fluid through said conduit from said supply source to said receiving location; a free flow detector associated with said peristaltic pump; said free flow detector comprising an alarm, a means for sensing the flow of fluid in said conduit, a means for sensing the rotation of said peristaltic pump and a means for comparing said sensed flow with said sensed rotation whereby if flow is sensed while said pump is not rotating, said alarm will be initiated to indicate such free flow condition.

8. A peristaltic pump for pumping a flow of fluid, having a tube, a motor, a rotor, and a free-flow detection system comprising:

means for sensing said fluid flow through said tube of said peristaltic pump;

means for sensing rotation of said rotor;

microprocessor for comparing said sensed fluid flow and said sensed rotor rotation against a predetermined criteria, such that a free-flow condition is identified;

an alarm electrically connected to said microprocessor and immediately activated by said microprocessor when the free flow condition is identified.

9. The peristaltic pump of claim 8, wherein said means for sensing fluid flow includes a drip chamber attached to said tube and a drip detector for sensing drops of said fluid in said chamber.

10. The peristaltic pump of claim 8, wherein said means for sensing rotation of said rotor includes a motor detector for sensing operation of said motor.

11. The peristaltic pump of claim 8, wherein said means for sensing rotation of said rotor includes an optical transmitter, an optical sensor, and an optical interrupting disc integrally connected to the rotor and positioned between the optical transmitter and the optical sensor.

12. The peristaltic pump of claim 8, wherein said microprocessor includes a program which activates said alarm when fluid flow is sensed and rotor rotation is not detected.

13. The peristaltic pump of claim 12, wherein said alarm is activated when said rotation of said rotor is not sensed and said drip detector senses more than one said drop of said fluid flow.

14. The peristaltic pump of claim 12, wherein said alarm is activated when said rotation of said rotor is not sensed and said drip detector senses more than five said drops of said fluid flow.

15. A peristaltic pump system for controlling a flow of fluid from a fluid source to a patient, said system having fluid source, a fluid tube, a drip chamber connected to the tube, a motorized rotor which intermittently rotates to compress the tube and thereby cause pumping action of fluid through the tube, and a free-flow detection system comprising:

a fluid flow sensor for detecting fluid flow through the fluid tube by detecting drops of fluid in the drip chamber;

a pump operation sensor for detecting the intermittent rotation of said rotor;

an alarm;

a microprocessor electrically connected to said fluid flow sensor and to said pump operation sensor and to said alarm;

said microprocessor having a programmed criteria for detecting a free flow condition and immediately activate said alarm when rotor rotation is not sensed by said pump operation sensor-while a predetermined number of drops of fluid are detected in said drip chamber by said fluid flow sensor.

16. A peristaltic pump system according to claim 15, wherein said programmed criteria of said predetermined number of drops of fluid is any number greater than one drop.

17. A peristaltic pump system according to claim 15, wherein said programmed criteria of said predetermined number of drops of fluid is any number greater than five drops.

* * * * *